US00PP27788P3

(12) United States Plant Patent
Carter

(10) Patent No.: US PP27,788 P3
(45) Date of Patent: Mar. 14, 2017

(54) ***SALVIA* PLANT NAMED 'IGNITION PURPLE'**

(50) Latin Name: *Salvia×jamensis*
Varietal Denomination: Ignition Purple

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 86 days.

(21) Appl. No.: 14/545,438

(22) Filed: May 4, 2015

(65) Prior Publication Data

US 2016/0330897 P1 Nov. 10, 2016

(51) Int. Cl.
*A01H 5/02* (2006.01)

(52) U.S. Cl.
USPC ..... Plt./475

(58) Field of Classification Search
USPC ..... Plt./475, 226
See application file for complete search history.

(56) References Cited

PUBLICATIONS

National Gardening Viewing post #611933 by Marilyn, My Mail Order plants for 2014, retrieved on Sep. 20, 2016, retrieved from the Internet at <http://garden.org/thread/view_post/611933/> 2 pp.*

* cited by examiner

*Primary Examiner* — June Hwu
(74) *Attorney, Agent, or Firm* — Bethany R. Roahrig; Barbara Campbell; Cochran Freund & Young, LLC

(57) ABSTRACT

A new cultivar of *Salvia* named 'Ignition Purple' that is distinguishable by intense vibrant deep purple flowers which are borne on compact plants with mid-green glossy leaves, is disclosed.

3 Drawing Sheets

Genus and species: *Salvia×jamensis.*
Variety denomination: 'Ignition Purple'.

BACKGROUND

The present disclosure relates to a new and distinct cultivar of *Salvia* plant, also known as a sage, a perennial that is grown for use as an ornamental landscape and container plant. The new variety is known botanically as *Salvia×jamensis* and will be referred to hereinafter by the cultivar name 'Ignition Purple'.

'Ignition Purple' originated and was selected from a large population of hybrid seedlings from a *Salvia* breeding program which was started in 2009. The breeding program was conducted in a greenhouse nursery in Elk, Calif. A controlled hybridization was carried out in 2012 using pollen collected en masse from many proprietary selections. The identity of the male parent is unknown. The collected pollen was applied to the flowers of *Salvia×jamensis* 'Mes Azur', also known as 'Mesa Azure' (U.S. Plant Pat. No. 21,097).

Seeds from this hybridization were sown and a single plant was selected in 2013 for its intense vibrant deep purple flowers which are borne on compact plants with mid-green glossy leaves, and was subsequently named 'Ignition Purple'.

'Ignition Purple' was first asexually propagated in early spring of 2013 in a greenhouse at the inventors nursery in Elk, Calif. using softwood tip cuttings. 'Ignition Purple' is stable and reproduces true to type in successive generations of asexual reproduction.

SUMMARY

The following traits have been repeatedly observed and represent the distinguishing characteristics of 'Ignition Purple'. 'Ignition Purple' has not been tested under all possible conditions and phenotypic differences may be observed with variations in environmental, climatic, and cultural conditions, without however, any variance in genotype.

1. 'Ignition Purple' exhibits a compact well-branched upright plant habit;
2. The flowers of 'Ignition Purple' are intense vibrant purple in color; and
3. 'Ignition Purple' grows and flowers rapidly. Flowering plants may be produced in 10 to 12 weeks from a cutting.

DESCRIPTION OF THE PHOTOGRAPHS

The accompanying color photographs illustrate the overall appearance of the new *Salvia* cultivar 'Ignition Purple' showing the colors as true as it is reasonably possible to obtain in colored reproductions of this type. Photographs were taken in April, 2015 in Santa Barbara, Calif. of three-month old plants grown outdoors in quart containers, with one pinch after initial cutting establishment and without any chemical growth regulators. Colors in the photographs may differ from the color values cited in the detailed botanical description, which more accurately describes the actual colors of the new variety 'Ignition Purple'.

DESCRIPTION OF THE NEW VARIETY

Figure 1:
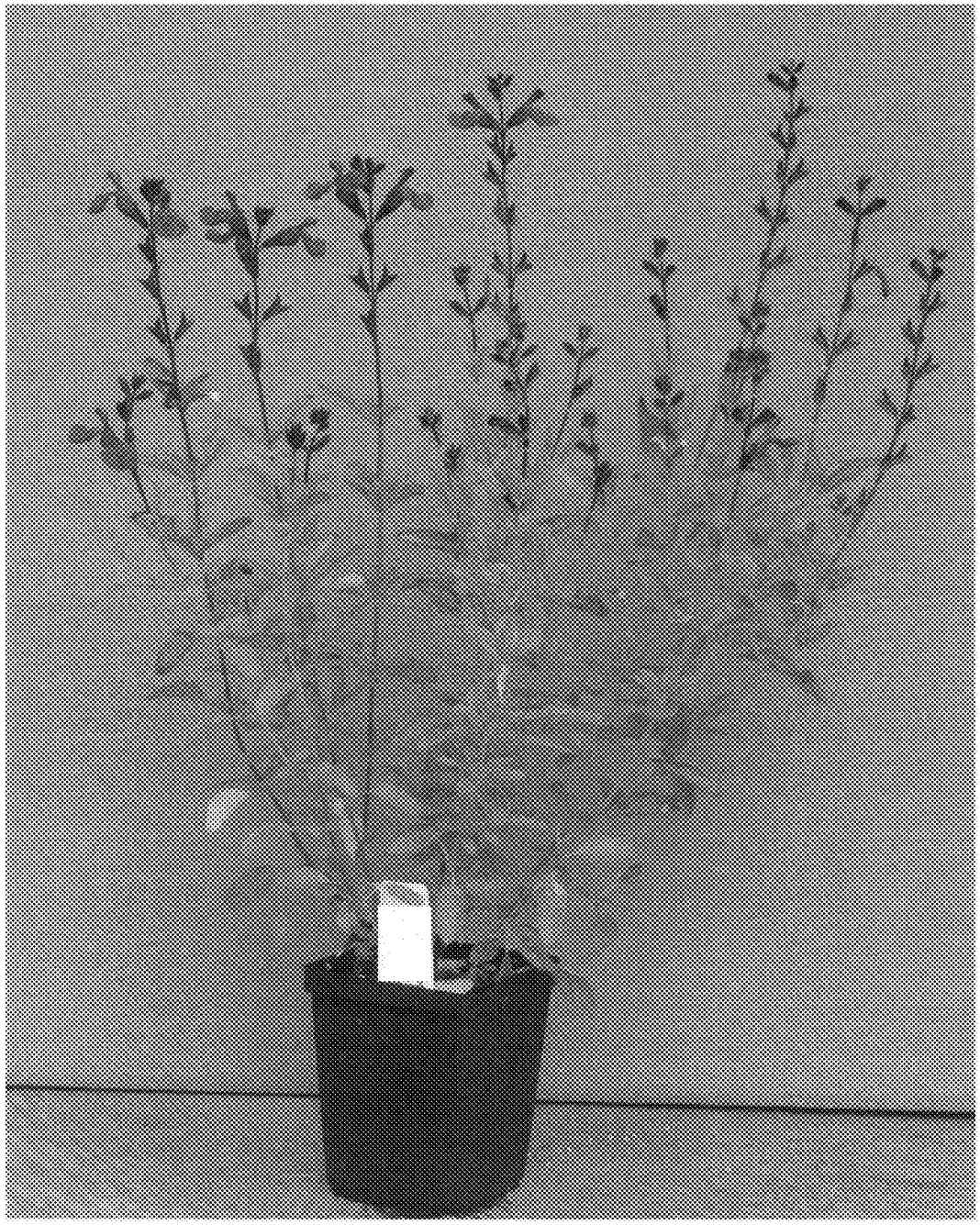
FIG. 1 depicts an entire plant in flower of 'Ignition Purple'.
Figure 2:
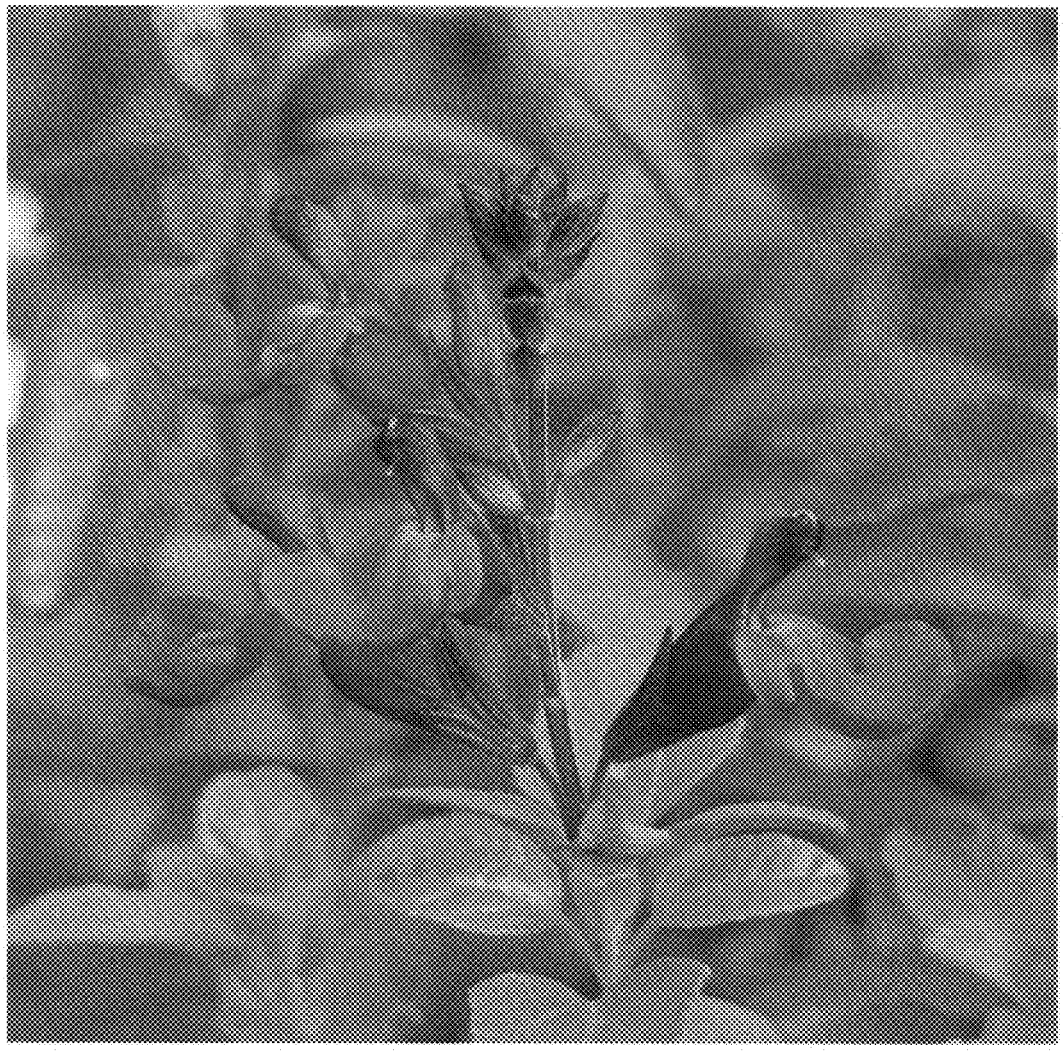
FIG. 2 depicts a close-up view of the inflorescence of 'Ignition Purple'.
Figure 3:
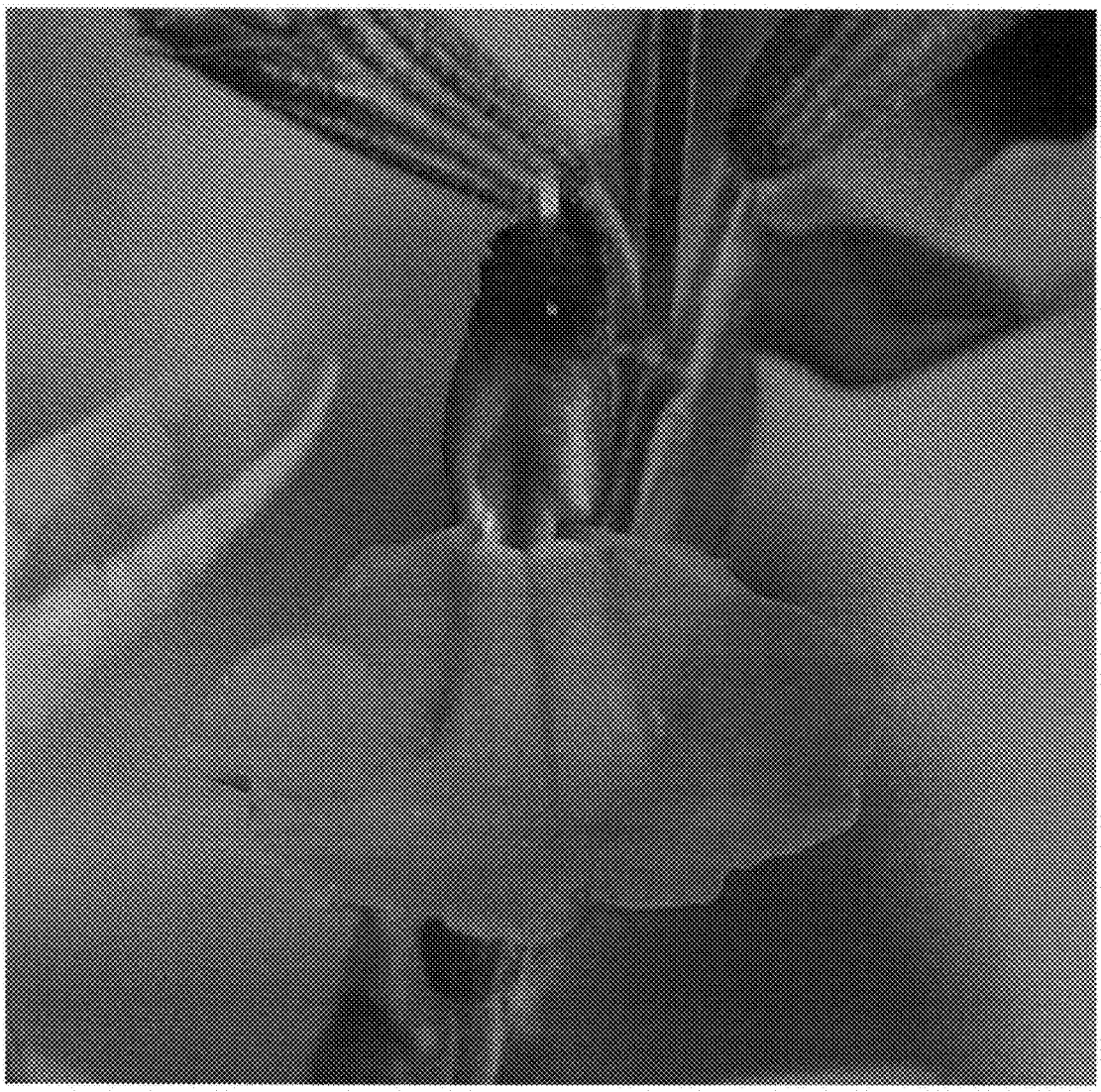
FIG. 3 depicts a close-up view of an individual flower of 'Ignition Purple'.

The following detailed descriptions set forth the distinctive characteristics of 'Ignition Purple'. Observations, measurements, values, and comparisons were collected in March and April, 2015 in Santa Barbara, Calif. from two to three-month old plants grown outdoors in full sun in quart sized containers in Elk, Calif., with one pinch after initial cutting establishment and without any chemical growth regulators. Plants were transferred to Santa Barbara, Calif. when in bud and observed through flowering. Color determinations were made in accordance with The 2007 Royal Horticultural Society Colour Chart from London England, except where general color terms of ordinary dictionary significance are used.

Classification:

*Family*.—Lamiaceae.
*Genus*.—*Salvia*.
*Species*.—×*jamensis*.
*Common name*.—Sage.

Parentage:

*Female parent*.—*Salvia*×*jamensis* 'Mes Azur' (U.S. Plant Pat. No. 21,097).
*Male parent*.—Unknown.

Plant:

*Propagation method*.—Softwood tip cuttings.
*Rooting system*.—Fine and fibrous.
*Vigor*.—Moderate vigor.
*Time to develop roots*.—5 days are needed for a cutting to develop roots at recommended rooting temperature of 20° to 22° Centigrade.
*Crop time*.—Approximately 12 weeks are required to produce a budded and flowering plant in a quart container from a rooted cutting.
*Suggested container size*.—Quart to 1 gallon container.
*Use*.—Ornamental for use as a landscape plant or container plant.
*Type*.—Perennial.
*Overall dimensions*.—After one year's growth in a 3.5 inch container: 30 cm to 40 cm in height, including the inflorescence, and 15 cm in width.
*Cultural requirements*.—Grow in full sun with moderate water and well-draining soil.
*Hardiness*.—USDA Zone 7.
*Form*.—Bush.
*Growth habit*.—Compact.
*Blooming season*.—From one month after breaking spring dormancy to first frost.
*Lastingness of blooms*.—Inflorescence has some flower for 14 days, individual flowers last for 2 to 3 days.

Stems (below first pinch):

*Length*.—1 cm to 2 cm.
*Diameter*.—4 mm.
*Color*.—174C, bark where formed, 174A.
*Shape*.—Square, edges rounded.
*Texture*.—Rough where lignified.

Branches:

*Quantity*.—8 to 12.
*Shape*.—Square.
*Length*.—18 cm to 22 cm.
*Width*.—1.5 mm to 2.0 mm.
*Internode length*.—1.5 cm.
*Color*.—178A close to stem, becoming green 144C towards apex.

Leaves:

*Type, arrangement*.—Simple, opposite.
*Attachment*.—Petiolate.
*Quantity per branch*.—8 to 10 pairs.
*Shape*.—Elliptic.
*Length*.—22 mm.
*Width*.—10 mm.
*Margin*.—Weakly undulating, shallowly crenulate, entire towards base.
*Thickness*.—Slightly fleshy.
*Venation*.—Pinnate, midrib slightly sulcate.
*Texture*.—Adaxial surface: Glabrous, glossy. Abaxial surface: Glabrescent.
*Color*.—Adaxial surface: 143A. Abaxial surface: 143C.
*Apex*.—Acute.
*Base*.—Cuneate.
*Fragrance*.—Pleasant sage fragrance when rubbed.
*Stipules*.—Present in pairs at each leaf axil. Small, sessile, elliptic, 7 mm to 8 mm in length, 3 mm in width. All other characteristics same as leaves.

Petiole:

*Shape*.—Terete.
*Length*.—7 mm.
*Width*.—1 mm.
*Texture*.—Puberulent.
*Color*.—Young growth, 143C; older growth towards base, 178A.

Peduncle:

*Length*.—1.5 cm to 1.8 cm.
*Shape*.—Square.
*Width*.—1.0 mm to 1.2 mm.
*Texture*.—Puberulent.
*Color*.—N77A.

Inflorescence:

*Type*.—Terminal raceme. Flowers arranged in pairs, opposite, each pair rotate by 90 degrees.
*Length*.—6.0 cm to 7.5 cm.
*Diameter*.—5 cm.

Pedicel:

*Length*.—5 mm to 8 mm.
*Width*.—0.8 mm.
*Texture*.—Puberulent.
*Color*.—N77A.

Calyx:

*Shape*.—Campanulate, flared toward the apex.
*Length*.—10 mm.
*Height*.—4 mm.
*Width*.—2 mm.

Sepals:

*Quantity*.—2, one upper, one lower, substantially longitudinally fused.
*Length*.—10 mm.
*Width*.—6 mm when flattened.
*Shape*.—Boat shaped.
*Apex*.—Acuminate.
*Base*.—Truncate.
*Margin*.—Entire.
*Texture*.—Adaxial surface: Puberulent, longitudinally ribbed. Ribs 1 mm apart, raised less than 0.1 mm. Abaxial surface: Glabrous, longitudinal depressions.
*Color*.—Adaxial surface: 200A, ribs N186A. Abaxial surface: 144B becoming 200A towards (5 mm from) apex; longitudinal depressions N77A.

Flowers:

*Quantity*.—8 to 10 opposite pairs.
*Shape*.—Tubular, two-lipped.
*Fragrance*.—Pleasant sage fragrance.

Bud (as emerges from calyx, before petals differentiated):

*Shape*.—Ellipsoidal.

*Length.*—4 mm to 5 mm.
*Width.*—3 mm to 4 mm.
*Texture.*—Pubescent, especially apex which already bears cluster of hairs of upper petal lip.
*Color.*—N79B and N79A (cluster of hairs at apex).

Corolla:
*Shape.*—Tubular proximally to two-lipped distally, lower lip attitude relative to corolla is downward.
*Length.*—1.8 cm.
*Width.*—3 mm.
*Texture.*—Glossy, glandular.
*Color* (*both surfaces*).—77A, except tube base, which is white, translucent.

Petals:
*Quantity.*—2.
*Arrangement.*—One upper petal and one lower petal which appears as a large prominent lip with two lateral lobes fused to the lip and to each other.
*Upper petal.*—Shape: Hooded. Length: 9 mm to 10 mm. Width: 4 mm. Texture: Adaxial surface: Puberulent. Abaxial surface: Glabrous, with two longitudinal ribs. Apex: Rounded, with cluster of fine hairs approximately 1 mm in length, color N79A. Base: Truncate with lower lip at corolla mouth. Margin: Smooth, entire. Color: Adaxial surface: 77A. Abaxial surface: 85D except ribs and margin 77A.
*Lower petal, lip.*—Shape: Rhomboid, concave. Length: 6 mm. Width: 14 mm to 16 mm. Texture: Adaxial surface: Smooth. Abaxial surface: Smooth, glabrous, semi-glossy. Apex: Emarginate, depth of notch 1.5 mm. Base: Truncate. Margin: Gently undulating, entire except emarginated apex. Color: Adaxial surface: 83B. Abaxial surface: Nearest to 83B but very intense and iridescent.
*Lower petal, lateral lobes.*—Shape: Elliptic, fused at base, the pair appear as wings. Length (each lateral lobe): 6 mm. Width: 3 mm to 4 mm. Texture: Adaxial surface: Smooth. Abaxial surface: Smooth, glabrous, semi-glossy. Apex: Rounded. Base: Truncate, tiny hairs clustered towards and at the base. Margin: Smooth, entire except for hairs at the base. Color: Adaxial surface: 83B. Abaxial surface: Nearest to 83B but very intense and iridescent.

Floral bracts:
*Arrangement.*—Occasionally present singly or in pairs at base of flower.
*Shape.*—Ovate.
*Length.*—4 mm to 6 mm.
*Width.*—2 mm to 3 mm.
*Color* (*both surfaces*).—N186A with striations colored N187B.
*Apex.*—Acute.
*Margin.*—Entire.
*Persistence.*—Bracts are not persistent.

Reproductive organs:
*Stamens.*—Quantity: 1, comprised of two connected filaments, fused at base and longitudinally. Length: 15 mm. Color: NN155C.
*Filament.*—Length: Each filament is 14 mm, fused for 6 mm and free for 8 mm. Color: NN155D where free and 77A where connected.
*Anther.*—Length: 2 mm. Width: 0.5 mm. Color: 163B.
*Pollen.*—Amount: Sparse. Color: 163B.
*Pistil.*—Quantity: 1. Stigma: Shape: Asymmetrically forked. Length: Longer fork 4 mm, strongly recurved; shorter fork 2 mm, gently recurved. Width: 0.5 mm. Color: 84A. Style: Length: 25 mm. Color: NN155D, translucent.
*Ovary* (*only observed unfertilized, one pair of immature achenes*).—Length: 3 mm. Width: 1.5 mm. Color: 10B, achenes 8A.

Seed set: Rarely observed. Where present, one or two seeds per flower pollinated. Shape is ovoid, length 2 mm to 3 mm, diameter 1.5 mm. Color is black 203A. Surface is smooth and matte.

Disease and pest susceptibility: Susceptible to sucking insects when stressed. Generally outgrows most bacterial and viral infections. Resistant to deer and rabbit grazing.

Drought tolerance: Drought tolerant.

COMPARISON WITH PARENTAL LINES AND KNOWN VARIETY

'Ignition Purple' is distinguishable from the female parent, 'Mes Azur' as follows: 'Ignition Purple' bears smaller leaves which are also thicker, and grows with a denser plant habit with better branching. In addition, whereas the flowers of 'Ignition Purple' are an intense deep purple in color, the flowers of 'Mes Azur' are soft and muted purple in color.

'Ignition Purple' is similar to 'Sunsaruoro' (U.S. Plant Pat. No. 15,141), however the flowers of 'Sunsaruoro' are a light purple in color whereas the flowers of 'Ignition Purple' are a deep and vibrant purple in color.

I claim:

1. A new and distinct cultivar of *Salvia* plant named 'Ignition Purple' as described and illustrated herein.

* * * * *